(12) United States Patent
Srinivasa

(10) Patent No.: US 7,188,032 B2
(45) Date of Patent: Mar. 6, 2007

(54) INCREMENTAL DETERMINATION OF TEIRESIAS PATTERNS

(75) Inventor: Deepak M. Srinivasa, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 49 days.

(21) Appl. No.: 11/172,188

(22) Filed: Jun. 30, 2005

(65) Prior Publication Data

US 2007/0005259 A1   Jan. 4, 2007

(51) Int. Cl.
    *G06F 15/16* (2006.01)
(52) U.S. Cl. ......................................... 702/19; 709/230
(58) Field of Classification Search ................. 702/19, 702/20, 81, 182–185; 709/230
    See application file for complete search history.

(56) References Cited

U.S. PATENT DOCUMENTS

| 5,809,499 | A  | 9/1998  | Wong et al. |
| 6,373,971 | B1 | 4/2002  | Floratos et al. |
| 6,434,488 | B1 | 8/2002  | Robson |
| 6,446,011 | B1 | 9/2002  | Floratos et al. |
| 6,571,199 | B1 | 5/2003  | Floratos et al. |
| 6,571,230 | B1 | 5/2003  | Parida |
| 6,665,572 | B2 | 12/2003 | Buervenich et al. |
| 2002/0087495 | A1 | 7/2002 | Wang et al. |
| 2003/0023591 | A1 | 1/2003 | Ma et al. |
| 2003/0046010 | A1 | 3/2003 | Parida |
| 2003/0220771 | A1* | 11/2003 | Vaidyanathan et al. ........ 703/2 |
| 2004/0088722 | A1 | 5/2004 | Peker |
| 2005/0095597 | A1* | 5/2005 | Abdeen Hussan ............. 435/6 |

OTHER PUBLICATIONS

Burgard et al.; Review of the Tieresias-Based TTOLS of the IBM Bioinformatics and Pattern Discovery Group; Metabolic Engineering 3, 285-288 (2001).

Rigoutsos et al.; Combinatorial Pattern Discovery in Biological Sequences: The Teiresias Algorithm; Bioinformatics vol. 14, No. 1, 1998, pp. 55-67.

* cited by examiner

*Primary Examiner*—Edward Raymond
(74) *Attorney, Agent, or Firm*—Schmeiser, Olsen & Watts; William H. Steinberg

(57) ABSTRACT

A method for determining Teiresias patterns. Provided as input to the method are: a set $S'_0$ of n sequences denoted as $S_1, S_2, \ldots S_n$; positive integers L, W, and K; and Teiresias patterns $P'_0$ consisting of all <L, W, K> patterns for the set $S'_0$. Each sequence of the n sequences consists of characters from an alphabet. A sequence index i equals 1. A sequence $S_{n+1}$ is supplied to form a set $S'_i$ consisting of $S'_{i-1} \cup S_{n+1}$, where $S_{n+1}$ consists of characters from the alphabet. The Teiresias patterns $P'_i$ are determined by performing an algorithm that utilizes $S'_{i-1}$, L, W, K, $P'_{i-1}$, and $S_{n+i}$ as input. The Teiresias patterns $P'_i$ consist of all <L, W, K> patterns for the set $S'_i$.

30 Claims, 5 Drawing Sheets

INCREMENTAL DETERMINATION OF TEIRESIAS PATTERNS

BACKGROUND OF THE INVENTION

1. Technical Field

The present invention relates to a method for determining Teiresias patterns and more particularly to a method for incrementally determining Teiresias patterns.

2. Related Art

Pattern discovery methods for solving problems in computational biology are fast becoming a tool of choice. The standard Teiresias algorithm is a powerful pattern discovery tool that uses a combinatorial method to discover rigid patterns in a given set of sequences according to the specified parameters.

However, determining Teiresias patterns by direct execution of the standard Teiresias algorithm may be inefficient for circumstances in which sequences of Teiresias patterns are to be successively computed. Thus, there is a need for a more efficient method of determining Teiresias patterns than exists in the prior art for circumstances in which sequences of Teiresias patterns are to be successively computed.

SUMMARY OF THE INVENTION

The present invention provides a method for determining Teiresias patterns, said method comprising the steps of:

providing a set $S'_0$ of n sequences denoted as $S_1, S_2, \ldots S_n$, positive integers L, W, and K, and Teiresias patterns $P'_0$ consisting of all <L, W, K> patterns for the set $S'_0$, each sequence of the n sequences consisting of characters from an alphabet, wherein a sequence index i equals 1;

supplying a sequence $S_{n+1}$ to form a set $S'_i$ consisting of $S'_{i-1} \cup S_{n+1}$, wherein $S_{n+1}$ consists of characters from the alphabet; and determining Teiresias patterns $P'_i$ consisting of all <L, W, K> patterns for the set $S'_i$ by performing an algorithm that utilizes $S'_{i-1}$, L, W, K, $P'_{i-1}$, and $S_{n+i}$ as input.

The present invention provides a computer program product, comprising a computer usable medium having a computer readable program code embodied therein, said computer readable program code comprising an algorithm adapted to implement a method for determining Teiresias patterns, said method comprising the steps of:

providing a set $S'_0$ of n sequences denoted as $S_1, S_2, \ldots S_n$, positive integers L, W, and K, and Teiresias patterns $P'_0$ consisting of all <L, W, K> patterns for the set $S'_0$, each sequence of the n sequences consisting of characters from an alphabet, wherein a sequence index i equals 1;

supplying a sequence $S_{n+1}$ to form a set $S'_i$ consisting of $S'_{i-1} \cup S_{n+1}$, wherein $S_{n+1}$ consists of characters from the alphabet; and determining Teiresias patterns $P'_i$ consisting of all <L, W, K> patterns for the set $S'_i$ by performing an algorithm that utilizes $S'_{i-1}$, L, W, K, $P'_{i-1}$, and $S_{n+i}$ as input.

The present invention provides a process for integrating computing infrastructure, said process comprising integrating computer-readable code into a computing system, wherein the code in combination with the computing system is capable of performing a method for determining Teiresias patterns, said method comprising the steps of:

providing a set $S'_0$ of n sequences denoted as $S_1, S_2, \ldots S_n$, positive integers L, W, and K, and Teiresias patterns $P'_0$ consisting of all <L, W, K> patterns for the set $S'_0$, each sequence of the n sequences consisting of characters from an alphabet, wherein a sequence index i equals 1;

supplying a sequence $S_{n+1}$ to form a set $S'_i$ consisting of $S'_{i-1} \cup S_{n+1}$, wherein $S_{n+1}$ consists of characters from the alphabet; and determining Teiresias patterns $P'_i$ consisting of all <L, W, K> patterns for the set $S'_i$ by performing an algorithm that utilizes $S'_{i-1}$, L, W, K, $P'_{i-1}$, and $S_{n+i}$ as input.

The present invention advantageously provides a more efficient method of determining Teiresias patterns than exists in the prior art for circumstances in which sequences of Teiresias patterns are to be successively computed.

DETAILED DESCRIPTION OF THE INVENTION

Figure 1:
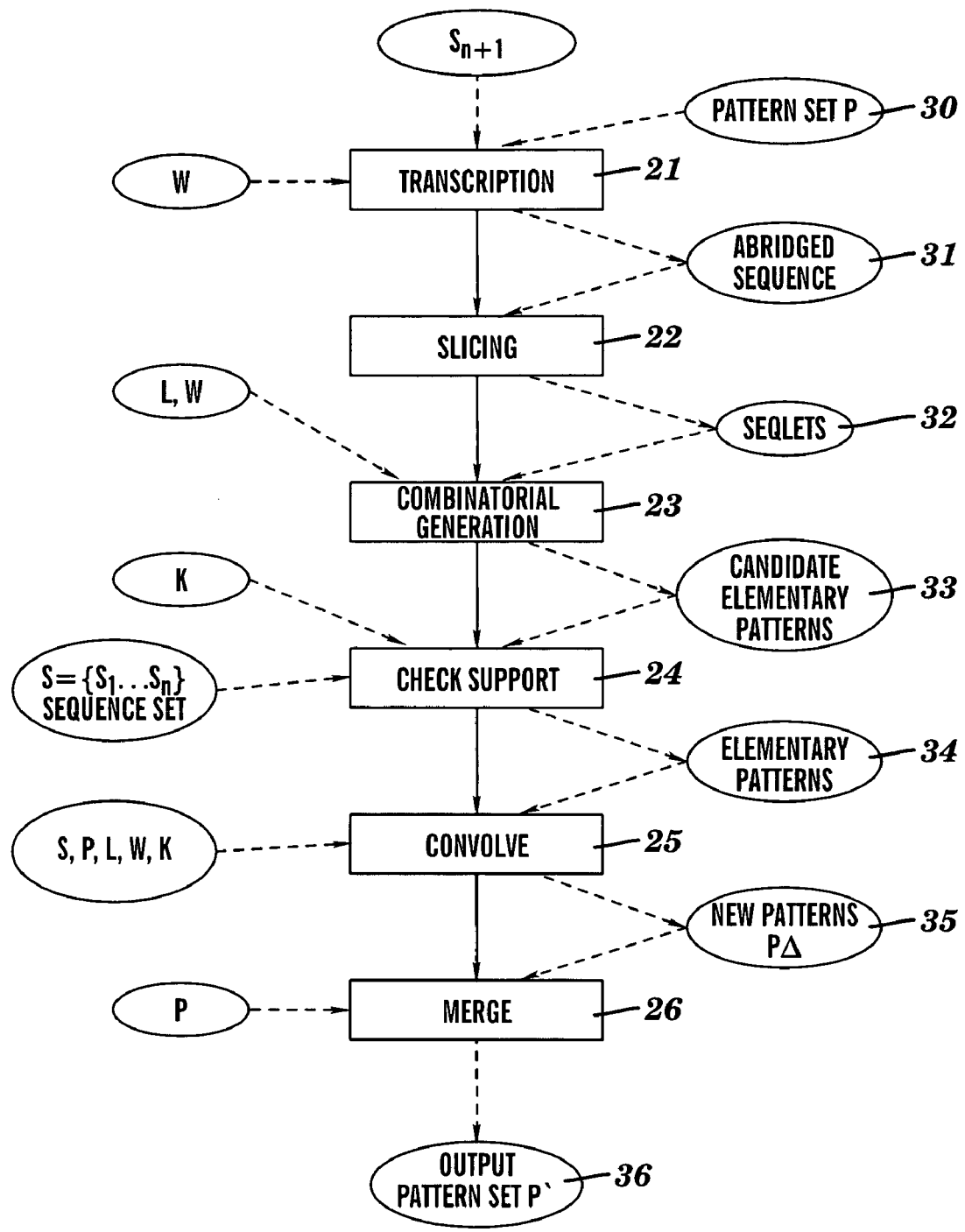
FIG. 1 is a high-level flow chart describing a method for incremental determination of Teiresias patterns, in accordance with embodiments of the present invention.

In certain pattern discovery applications (e.g., applications involve clustering) it is useful to incrementally discover the Teiresias patterns. The Teiresias patterns are the output patterns obtained from execution of the standard Teiresias algorithm. The Teiresias patterns may be obtained via direct execution of the standard Teiresias algorithm. The present invention discloses an alternative method for determining Teiresias patterns, namely a method for determining Teiresias patterns incrementally for a set of n+1 given sequences. In accordance with the present invention, a set of n sequences is supplied along with their corresponding Teiresias patterns. The Teiresias patterns corresponding to the supplied n sequences may be determined by, inter alia, direct execution of the standard Teiresias algorithm. If a $(n+1)^{th}$ sequence is additionally supplied, the present invention efficiently computes, without directly executing the standard Teiresias algorithm, the new Teiresias pattern set corresponding to the updated set of (n+1) sequences. The updated set of (n+1) sequences consists of the original n sequences and the additional $(n+1)^{th}$ sequence. Thus, the Teiresias patterns associated with the updated set of (n+1) sequences are calculated more efficiently by the algorithm of the present invention than by direct execution of the standard Teiresias algorithm.

The remaining portion of the detailed description is presented infra in four sections. The first section (Section 1) provides a description of the standard Teiresias algorithm. The second section (Section 2) provides a description of the incremental determination of Teiresias patterns in accordance with the present invention. The third section (Section 3) provides an example illustrating incremental determination of Teiresias patterns in accordance with the present invention. The fourth section (Section 4) provides a description of a computer system which may be used to incrementally determine Teiresias patterns in accordance with the present invention.

1. The Standard Teiresias Algorithm

Given a set S of input sequences, and three parameters L, W and K (defined infra), the standard Teiresias algorithm discovers patterns called Teiresias patterns which are rigid patterns. Teiresias belongs to the genre of pattern discovery algorithms which are capable of detecting and reporting all existing patterns in a set of input sequences without enumerating the entire solution space and without using alignment. Furthermore, the patterns reported are maximal, i.e., they are as specific as possible. Formally, a pattern P is more specific than a pattern Q if any sequence which matches P also matches Q (e.g., the pattern XYZ is more specific than the pattern X.Z). A pattern P in the set S of input sequences is maximal if there is no other pattern in S more specific than P with the same number of occurrences as P.

The standard Teiresias algorithm utilizes the followings definitions and assumptions:

1. A sequence is a string of characters from a specific alphabet. For example, an amino acid is a sequence of characters from the nucleotide alphabet (A, C, G and T). The alphabet gives all the characters that a sequence can have. The sequences can be of arbitrary length. A set of such sequences is given as input to the standard Teiresias algorithm.
2. The characters in the sequence may each represent a residual structural unit, called a residue, of a composite. An example of such composite is a molecular structure or complex molecule such as a protein molecule (e.g., an amino acid residue from hydrolysis of protein).
3. A dot (.) is referred to as a "don't care" character. This means that any valid character from the alphabet can appear in its place.
4. A pattern is a string of characters that begins and ends with a letter (not a dot, but a character from the alphabet), and can have zero or more letters or dots in between. For example, AC..H is a pattern, but AC. is not (since it does not end with a letter). Note that the dots can be any character from the alphabet, and therefore, a pattern is a regular expression and represents a set of concrete strings. Thus for the example cited above, ACAGH, ACCCH, ACAHH are all valid strings represented by the pattern.
5. L, W and K are numbers provided by the user. L represents the number of letters and W represents sequence length (i.e., total number of characters in the sequence). Together, these two parameters L and W represent the density constraint. The parameter K represents support that a pattern must have in order to be reported to the user. Also, L<=W. An <L, W> pattern is one which will have L letters in any consecutive W characters of the pattern. This is a way to constrain the number of dots that appear in the pattern. For example, if L=3 and W=4, then it means that for any consecutive 4 characters in a pattern, there should be at least 3 letters (means there could be 0 or 1 dot in the pattern). So, AC.H is a <3, 4> pattern while A.C.H is not.
6. An <L, W, K> pattern is one which is an <L, W> pattern and appears in at least K sequences from the given input sequence set. K is called the support parameter.
7. An elementary pattern is an <L, W> pattern that contains exactly L residues. For example, if S={$s_1$=SDFBASTS, $s_2$=LFCASTS, $s_3$=FDASTSNP} then the set of all <3, 4> patterns with support at least 3 is {"F.AS", "AST", "AS.S", "STS", "A.TS"}.

Using the preceding definitions the standard Teiresias algorithm discovers the <L, W, K> patterns for the set of given sequences. The parameters L, W and K are provided by the user. There are two phases in the execution of the standard Teiresias algorithm: scanning and convolution. The scanning phase precedes the convolution phase.

The scanning phase scans all the sequences in the input set S and locates all elementary patterns with support at least K. Note that the standard Teiresias algorithm considers all the characters in the alphabet and resorts to a combinatorial approach of generating all the possible combinations of characters (with dots as well), for all possible sizes (constrained by the requirement that it should be an elementary pattern). For each of these combinations generated, the standard Teiresias algorithm checks for support in the given set of sequences. Those combinations that have the required support will be put into the generated elementary pattern set.

The convolution phase utilizes, as input, the set of elementary patterns generated in the scanning phase. In the convolution phase, these elementary patterns will be combined to form larger patterns. These larger patterns will then be checked for support and will be retained if they have the necessary support. These retained larger patterns will be used for further convolution to obtain yet bigger patterns. This process goes on recursively until all patterns are discovered. The way in which convolution occurs is described as follows.

Two patterns A and B can be pieced together to form a bigger pattern if the suffix of A is the same as the prefix of B. For example, F.AS and AST can be combined to form F.AST. Similarly, F.AST and STS can be combined to form F.ASTS. In this manner, larger patterns can be formed by convolution.

To make the description more formal, the two functions of prefix and suffix are defined. Let prefix(P) be the uniquely defined sub-pattern of P that has exactly (L−1) letters and is a prefix of P. Similarly, let suffix(P) be the uniquely identified sub-pattern of P that has exactly (L−1) letters and is a suffix of P. Thus, for given patterns P and Q if suffix(P) is the same as prefix(Q) then the resulting convolution pattern R will be PQ' where Q=prefix(Q)Q'. If the suffix and prefix do not match, then the convolution pattern will be null.

Using the preceding convolution process, the standard Teiresias algorithm methodically treats the set of patterns (starting from elementary patterns) until the final set of maximal patterns are obtained. The algorithm uses a stack based approach to process all the intermediate patterns. The standard Teiresias algorithm is available for public use at a website whose web address is a concatenation of "http" and "://cbcsrv.watson.ibm.com/Tspd.html".

The following illustrative example comprises Teiresias input of L=3, W=5, and K=2 along with the input sequences S1, S2, and S3 as shown in Table 1. The resultant output patterns from executing the standard Teiresias algorithm for this example are likewise $S_3$ shown in Table 1.

TABLE 1

| Input Sequences | Output Patterns |
| --- | --- |
| S1: ABCDEFGHIJKLMNOPQRSTUV | HIJKLMN |
| S2: AXCDXXXHIJKLMNXXQTUV | TUV |
| S3: ABCDEFGHIJKLMNOPUAHIJKLMNOXYZSTUV | A.CD |

TABLE 1-continued

| Input Sequences | Output Patterns |
| --- | --- |
| | HIJKLMNO |
| | ABCDEFGHIJKLM-NOP |
| | HIJKLMN..Q |
| | STUV |
| | HIJKLMN.X |

The standard Teiresias algorithm is explained in detail in the following references:

1) Floratos, A., and Rigoutsos, I. (1998). "Combinatorial pattern discovery in biological sequences: the TEIRESIAS algorithm", Bioinformatics, Vol 14, No. 1, 1998;
2) Anthony P. Burgard, Gregory L. Moore and Costas D. Maranas, "Review of the TEIRESIAS-Based Tools of the IBM Bioinformatics and Pattern Discovery Group", Metabolic Engineering 3, 285–288 (2001); and
3) Website address formed by concatenation of "http" and "://cbcsrv.watson.ibm.com/Tspd.html".

2. Incremental Determination of Teiresias Patterns

Let Σ be the alphabet of characters that can occur in the sequences. Given a set of n sequences, and three parameters L, W and K, the standard Teiresias algorithm discovers patterns with the following characteristics. A pattern is defined as any string that begins and ends with a character (from Σ), and contains an arbitrary combination of characters (from Σ) and '.' characters. The '.' character (referred to a as "don't care" character) is used to denote a position that can be occupied by an arbitrary character. For any pattern P, any substring of P that itself is a pattern is called a subpattern of P. For example, 'H..E' is a subpattern of the pattern 'A.CH.E'. A pattern P is called an <L, W> pattern (with L≦W) if every subpattern of P with length W or more contains at least L characters. A pattern P is called an <L, W, K> pattern if it is an <L, W> pattern and occurs in at least K sequences (from the given input sequence set). The standard Teiresias algorithm discovers all <L, W, K> patterns from the given input sequence set and reports only maximal patterns, as described supra.

The present invention incrementally determines the Teiresias patterns by a method having inputs and outputs listed in Table 2.

TABLE 2

Incremental Determination of Teiresias Patterns

| Inputs | Outputs |
| --- | --- |
| 1. Sequence Set S consisting of n sequences ($S_1$ to $S_n$). | 1. A pattern set Q that contains the Teiresias patterns that would have reported if the standard Teiresias algorithm were run on the sequence set S' = S ∪ {$S_{n+1}$} with parameters L, W, K. |
| 2. Teiresias parameters L, W and K | |
| 3. Pattern Set P that contains patterns discovered by standard Teiresias algorithm for the sequence set S with parameters L, W and K. | |
| 4. The extra sequence ($S_{n+1}$) to be added to the sequence set. | |

A set of n sequences ($S_1$ to $S_n$) and the corresponding Teiresias patterns are given to start with. Then, an additional sequence ($S_{n+1}$) is added to the sequence set. The problem is then to determine the new Teiresias pattern set that reflects the addition of this extra sequence ($S_{n+1}$). One straightforward approach is to run the standard Teiresias algorithm again with the n+1 sequences and rediscover all the Teiresias patterns. To do so, however, requires doing more work than is necessary. The problem solved by the present invention is to compute these new Teiresias patterns without running the standard Teiresias algorithm on the entire set, but to use the already discovered pattern set P for the n sequences ($S_1$ to $S_n$) and perform only the incremental computation required to discover the new pattern set P'. This is the approach taken with the present invention.

There can be several applications for such a method of the present invention. These techniques of the present invention will be useful in scenarios where the sequences will be generated one after another, and there is a need to study the patterns as the sequences are added. In such scenarios, it makes more sense to have an incremental algorithm rather than running the original algorithm over the entire data set all the time. In clustering applications, such as Expressed Sequence Tags (EST) clustering, Gene Sequencing, etc., there are occasions when a cluster would have its pattern set already discovered and new sequences might have to be added to the cluster, or that two clusters have to be merged. In such circumstances, the techniques of the present invention will prove to be useful. The techniques of the present invention can be used as a basis for clustering using Teiresias patterns.

The approach followed in the present invention is to compute the new elementary patterns that are generated due to the introduction of the $(n+1)^{th}$ sequence ($S_{n+1}$). An elementary pattern is a <L, W> pattern containing exactly L non-dot characters. The key here is to note that the entire n+1 sequences need not be considered for generating the elementary patterns, because the $(n+1)^{th}$ sequence ($S_{n+1}$) may already contain patterns from the pattern set P. In such a case, certain parts of the new sequence ($S_{n+1}$) can be intelligently ignored such that only a smaller portion of the new sequence ($S_{n+1}$) need be considered. This will reduce the number of elementary patterns generated and hence increase the performance of the algorithm of the present invention. Also, the generation of elementary patterns does not follow the combinatorial approach of the standard Teiresias algorithm because there is only one sequence ($S_{n+1}$) to deal with here. So, a sequential treatment is given to the sequence to generate the necessary promising elementary patterns. This also means that only the minimal work that is necessary for the incremental discovery is performed. Once the required elementary patterns are determined, these elementary patterns can be convolved with each other, and with the patterns in P, to form bigger patterns with the required support. The last element to be noted is that some of the patterns in P that are contained by the new sequence ($S_{n+1}$) may make the pattern more specific, and hence a few patterns of P might lose their maximality and new maximal patterns might be introduced. This case is also handled by the algorithm of the present invention.

FIG. 1 is a high-level flow chart describing a method comprising steps 21–26 for incremental determination of Teiresias patterns, in accordance with embodiments of the present invention. Steps 21–26, which are represented in rectangular boxes and described infra in detail are: transcription (step 21), slicing (step 22), combinatorial generation (step 23), check support (step 24), convolve (step 25), and merge (step 26).

In FIG. 1, the ovals represent data which are coupled to the process steps by directional lines. If the directional line points from an oval to a rectangular box process step, then the oval represents input data to the process step. If the directional line points from a rectangular box process step to an oval step, then the oval represents output data from the process step. Accordingly, the transcription step 21 accepts input data W, $S_{n+1}$, and pattern set P 30 and outputs an abridged sequence 31. The slicing step 22 accepts as input the abridged sequence 31 and outputs seqlets 32. The combinatorial generation step 23 accepts as input L,W, and seqlets 32 and outputs candidate elementary patterns 33. The check support step 24 accepts as input K, sequences $S_1 \ldots S_n$, and the candidate elementary patterns 33 and outputs elementary patterns 34. The convolve step 25 accepts as input S, P, L, W, K, and the elementary patterns 34 and outputs new patterns PΔ 35. The merge step 26 accepts as input the new patterns PΔ 35 and outputs the output pattern set P' 36.

The transcription step, slicing step, combinatorial generation step, check support step, convolve step, and merge step of FIG. 1 are discussed next in detail.

2.1 Transcription Step

The inputs to the transcription step 21 of FIG. 1 are the pattern set P, the next sequence $S_{n+1}$ and the Teiresias parameter W. The primary function of the transcription step 21 is to scan the sequence $S_{n+1}$, compute the patterns of P that are contained in $S_{n+1}$, and based on that computation, identify portions of $S_{n+1}$ that can really lead to new patterns. A character in the new sequence $S_{n+1}$ is said to be transcribed if it is considered for the generation of elementary patterns. Parts of $S_{n+1}$ are thus selected and a new sequence, called the abridged sequence, is generated for further processing. A character in $S_{n+1}$ will be transcribed if: 1) the character is not inside any pattern occurrence (occurrences of the patterns from $P_{next}$); and 2) the character and its $(W-1)^{th}$ character to the left or to the right do not occur in the same pattern. The reasoning behind checking for the above two conditions for transcribing is as follows. Any portion of a pattern occurrence in $S_{n+1}$ is already found to be a Teiresias pattern. Since the reported Teiresias patterns include only maximal patterns, it does not make sense to choose portions of already identified pattern occurrences. Even if these portions were to be chosen as possible candidates for elementary patterns, they would eventually result in the same pattern as already discovered by Teiresias during the convolution phase that comes later. Therefore, in order to minimize the work performed, the algorithm of the present invention neglects the portions of $S_{n+1}$ that are pattern occurrences of the patterns from the set $P_{next}$. $P_{next}$ is the set of patterns in P that occur in $S_{n+1}$. Therefore, only portions that are not inside any pattern occurrence are considered. However, there is an exception to this rule. The elementary patterns occurring at the boundaries of one or more patterns are to be considered because they are not a part of a single pattern, and hence will not already be handled by the standard Teiresias algorithm. Therefore, the present invention handles such patterns. This is the second case of transcription outlined supra. The essence here is to identify portions of the new sequence that is not already handled by the standard Teiresias algorithm.

Figure 2:
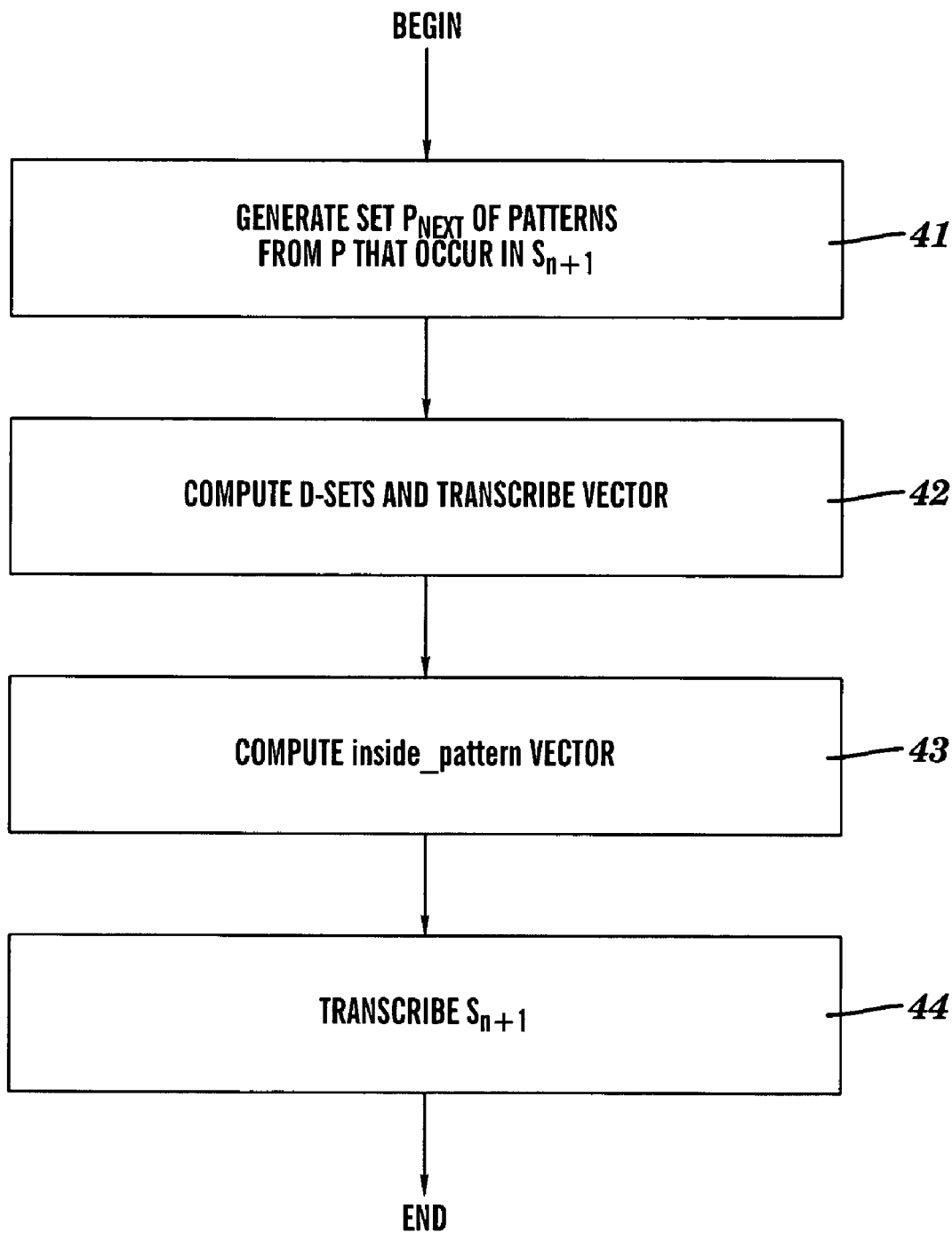
FIG. 2 is a flow chart for implementing the transcription step of FIG. 1, in accordance with embodiments of the present invention.

FIG. 2 is a flow chart comprising steps 41–44 which implement the transcription step 21 of FIG. 1, in accordance with embodiments of the present invention. Table 3 comprises pseudocode associated with steps 41–44 of FIG. 2, namely: generate a set $P_{next} \subseteq P$, such that all patterns in $P_{next}$ occur in $S_{n+1}$ (step 41); compute the D-sets and transcribe vector (step 42); compute inside_pattern vector (step 43); and transcribe $S_{n+1}$ (step 44).

TABLE 3

1. Generate a set $P_{next} \subseteq P$, such that all patterns in $P_{next}$ occurs in $S_{n+1}$.
2. Compute the D-sets and transcribe vector as follows
   Initialize vectors $D_{in}$, $D_{out}$ to zero values.
   For each pattern in $P_{next}$
      (let $P_i$ be the current pattern)
      Compute all occurrences of $P_i$ in $S_{n+1}$ into a vector O.
      ($O_t$ (begin) gives the offset of start position of the $t^{th}$ occurrence and $O_t$ (end) gives the offset of the end position of the $t^{th}$ occurrence)
      For each occurrence of $P_i$ in $S_{n+1}$
         Increment $D_{in}$ [$O_t$ (begin)]
         Increment $D_{out}$ [$O_t$ (end)]
      End For
   End For
   For i = 1 to length of $S_{n+1}$
      if (S(i) and S(i − W + 1) are in the same pattern) OR
         (S(i) and S(i + W − 1) are in the same pattern)
      then transcribe [i] = 1
      else transcribe [i] = 0
   (Note that if array indices on RHS go beyond limits, then they are restricted to the maximum or the minimum value appropriately)
3. Compute inside_pattern vector
   Initialize vector inside_pattern to zero
   For i = 1 to length of $S_{n+1}$
      inside_pattern [i] = inside_pattern [i − 1] + $D_{in}$ [i] − $D_{out}$ [i − 1]
   End For
   (Handle array index out of bounds appropriately)
4. Transcribe $S_{n+1}$
   Initialize abridged_sequence string to empty string
   For i = 1 to length of $S_{n+1}$
      if (inside_pattern [i] == 0 OR transcribe [i] > 0)
         add $S_{n+1}$ [i] to abridged_sequence
      else
         if last character of abridged_sequence is not 'X'
            add 'X' to abridged_sequence
   End For Step 41 identifies those patterns from P that occur in $S_{n+1}$ and puts said patterns in a set called $P_{next}$. For example if P={A.CG, TT.C, GAT, CC.GTA, TT.CT.AC.AC, CGACG, AAA.AT, GTGTG} and $S_{n+1}$=CTGATTCCTTACGACAGATTT, then $P_{next}$={TT.C, GAT, TT.CT.AC.AC}.

Steps 42 and 43 compute decision variables that will be used to determine whether a part of the sequence has to be transcribed or not. When a part of the sequence is transcribed, it means that there is a chance of finding <L, W, K> patterns in them against the set S'=S∪{$S_{n+1}$}. Since occurrences of patterns in $P_{next}$ on $S_{n+1}$, are already Teiresias patterns, there is no point in examining those regions (therefore they are not transcribed), except for the following two cases:

1. At the boundary areas of these pattern occurrences, some patterns can be found and should therefore not be neglected.
2. Due to the addition of $S_{n+1}$, some patterns in $P_{next}$ may become more specific and still hold support and therefore should also be considered.

In the transcription stage 21 of FIG. 1, case 1 above possibilities is handled, whereas case 2 is handled in later during the convolution step 25 of FIG. 12.

In step 42, three vectors (D-vectors and transcribe) are computed. These vectors are of the same size as $S_{n+1}$. The vector $D_{in}$ holds information about the starting points of the pattern occurrences (from $P_{next}$) in $S_{n+1}$. Thus, $D_{in}$[i] gives the number of pattern occurrences (from $P_{next}$) starting at location i on $S_{n+1}$. The vector $D_{out}$ holds information about the ending points of the pattern occurrences (from $P_{next}$) in $S_{n+1}$. Thus, $D_{out}$[i] gives the number of pattern occurrences (from $P_{next}$) ending at location i on $S_{n+1}$. The transcribe vector holds information about whether a character from the new sequence and its corresponding $(W-1)^{th}$ character to the left and to the right is occurring in two patterns or not.

In step 43, insidePattern vector is computed using the D-vectors. Using inside_pattern and transcribe vectors, the transcription is completed in step 44. The vector insidePattern will hold information about whether a particular character in the sequence $S_{n+1}$ is inside a pattern occurrence of $P_{next}$ or not. The vector transcribe will hold information about those areas inside pattern occurrences that should still be transcribed because of the possibility of finding elementary patterns in that region. An example of the transcription steps 41–44 is next provided.

Let $(n+1)^{th}$ sequence be $S_{n+1}$=CTGATTCCTTACGACA-GATTT. Let the Teiresias parameters given as input be L=3, W=4, K=3. Let the pre-discovered Teiresias patterns be P={A.CG, TT.C, GAT, CC.GTA, TT.CT.AC.AC, CGACG, AAA.AT, GTGTG}. In the step 41 of the transcription stage, $P_{next}$ is computed as follows: $P_{next}$={TT.C, GAT, TT.CT.A-C.AC}. The portions of $S_{n+1}$ that are covered by occurrences of patterns from $P_{next}$ are underlined in $S_{n+1}$ as follows: CT GATTCCTTACGACAGATTT. The D, inside_pattern and the transcribe vectors for this example are computed in steps 42–43 as shown in the Table 4.

TABLE 4

| $S_{n+1}$ | C | T | G | A | T | T | C | C | T | T | A | C | G | A | C | A | G | A | T | T | T |
|---|---|---|---|---|---|---|---|---|---|---|---|---|---|---|---|---|---|---|---|---|---|
| $D_{in}$ | 0 | 0 | 1 | 0 | 2 | 0 | 0 | 0 | 1 | 0 | 0 | 0 | 0 | 0 | 0 | 0 | 1 | 0 | 0 | 0 | 0 |
| $D_{out}$ | 0 | 0 | 0 | 0 | 1 | 0 | 0 | 1 | 0 | 0 | 0 | 1 | 0 | 0 | 1 | 0 | 0 | 0 | 1 | 0 | 0 |
| i_p | 0 | 0 | 1 | 1 | 3 | 2 | 2 | 2 | 2 | 2 | 2 | 2 | 1 | 1 | 1 | 0 | 1 | 1 | 1 | 0 | 0 |
| tr | 1 | 1 | 1 | 1 | 1 | 1 | 1 | 0 | 0 | 0 | 0 | 0 | 1 | 1 | 1 | 1 | 1 | 1 | 1 | 1 | 1 |

Note that in Table 4, i_p is an abbreviation for inside_pattern vector and tr is an abbreviation for transcribe vector. The output of the transcription stage will be the following abridged sequence: CTGATTCxGACAGATTT In this example, the reduction in the number of residues considered for generation of elementary patterns is 5. The length of $S_{n+1}$ is 21 and the length of the abridged sequence is 16. In general, the greater the reduction in length, the faster will be the incremental discovery. In cases where long patterns are present in $P_{next}$, the algorithm will yield better performance.

In the pseudo code description of the transcription stage given in Table 3 supra, the computation of the transcribe vector requires one to establish if a character of $S_{n+1}$ and its $(W-1)^{th}$ character to the left or right is present in the same pattern or not. An efficient ways to implement this part of the algorithm is to use the techniques Arithmetizing Set Theory, the application of which described briefly herein. This technique of using prime numbers for set member association was also used by Godel for the Godel numbering system. This technique is based on assigning prime numbers to set members, and then, utilizing the Fundamental Theorem of Arithmetic, the technique converts set theoretic operations to arithmetic operations. Here, in this algorithm, the non-occurrence of a pattern (which is considered as a default pattern) is associated with the first prime number 2. Then each occurrence of a pattern in $P_{next}$ in $S_{n+1}$ is assigned a successive prime number. Thus, in the example given above, the following prime numbers are assigned.

Occurrence of TT.C at location 5 is assigned prime number 3.

Occurrence of TT.C at location 9 is assigned prime number 5.

Occurrence of GAT at location 3 is assigned prime number 7.

Occurrence of GAT at location 17 is assigned prime number 11.

Occurrence of TT.CT.AC.AC at location 5 is assigned prime number 13.

Once these assignments are done, the transcribe vector can be computed as follows. First an intermediate vector called t' is computed as follows. The t' vector is of the same length as $S_{n+1}$. All elements of t' vector are initialized as shown in the pseudocode of Table 5.

TABLE 5

For all i from 1 to length of $S_{n+1}$
    if inside_pattern[i] >0 t`[i] = 1
    else t`[i] = 2
End For The pseudocode of Table 5 assigns all characters not occurring in any pattern to have the value of 2 (the first prime number) and all other elements to have a value of 1. The t' vector is then updated according to the pattern occurrences as shown in the pseudocode of Table 6.

TABLE 6

For all i from 1 to length of $S_{n+1}$
    If (inside_pattern [i] >0)
        //Handle all array index out of bounds appropriately
        If (inside_pattern [i-1] > 0)
            t`[i] = t`[i-i]
        End If
        If ($D_{in}$ [i] > 0)
            Find all pattern occurrences p which begin at i
            Let t`[i] =t`[i] *$p^r$ where $p^r$ is the prime number
            associated with that occurrence p.
        End If
        If ($D_{out}$ [i-1] > 0)
            Find all pattern occurrences p which end at i
            Let t`[i] = t`[i]/$p^r$ where pr is the prime number
            associated with that occurrence p.
        End If
    End If
End For Once the t' vector is computed in the preceding manner, the transcribe vector can be efficiently computed as shown in the pseudocode of Table 7.

TABLE 7

If (gcd(t`[i], t`[i-W+1])=1) OR gcd(t`[i],
    t`[i+W-1]))
    transcribe [i] = 1
Else
    transcribe [i] = 0
End If Note that the gcd (a, b) function in the pseudocode of Table 7 returns the greatest common divisor of a and b. Also note that array index out of bounds conditions are appropriately handled. The vector t' for the running example is computed as follows. Note that in the following Table 8, tr is an abbreviation for transcribe vector.

TABLE 8

| $S_{n+1}$ | C | T | G | A | T | T | C | C | T | T | A | C | G | A | C | A | G | A | T | T | T |
|---|---|---|---|---|---|---|---|---|---|---|---|---|---|---|---|---|---|---|---|---|---|
| t` | 2 | 2 | 7 | 7 | 273 | 39 | 39 | 39 | 65 | 65 | 65 | 65 | 13 | 13 | 13 | 2 | 11 | 11 | 11 | 2 | 2 |
| tr | 1 | 1 | 1 | 1 |  | 1 | 1 | 1 | 0 | 0 | 0 | 0 | 1 | 1 | 1 | 1 | 1 | 1 | 1 | 1 | 1 |

The output of the transcription process will be an abridged sequence as shown for the example above. Further processing will next be done on this abridged sequence. The portion of the new sequence that was not transcribed will not be used for pattern discovery at all.

2.2 Slicing Step

Figure 3:
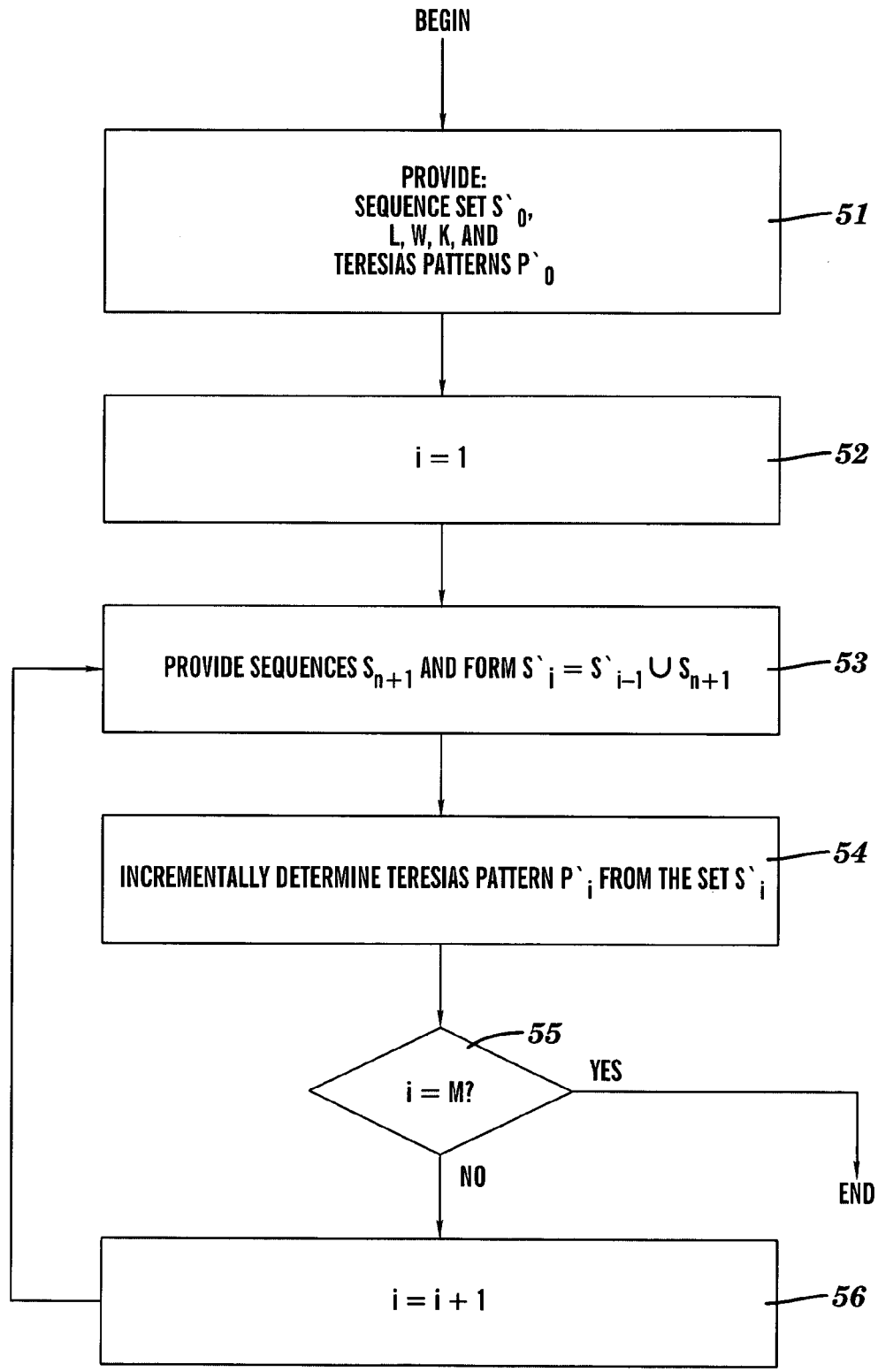
FIG. 3 is a flow chart describing a process for incrementally determining Teiresias patterns associated with successively added sequences to a base set of sequences, in accordance with embodiments of the present invention.

The slicing step 22 of FIG. 1 scans the abridged sequence, and splits the abridged sequence by the marker 'x' that has been produced in step 44 the transcription process (see FIG. 3 and Table 3). An example of slicing is as follows.

Input Abridged Sequence: ATTGxTTGGGTGxTGxACAGxCCG

Output Seqlets After Slicing: Seqlets={ATTG, TTGGGTG, TG, ACA, CCG}

Each of these individual seqlets are next used in the generation of candidate elementary patterns.

2.3 Combinatorial Generation Step

In the combinatorial generation step 23 of FIG. 1, the seqlets are individually scanned from left to right, and all possible combinations of <L,W> elementary patterns are generated for each seqlet. Note that an <L,W> elementary pattern will have exactly L residues. In the standard Teiresias algorithm, the number of sequences are large and the alphabet is small. Therefore the approach taken in the standard Teiresias algorithm is to combinatorially generate all possible <L,W> elementary patterns over the alphabet, without regard to the input sequences given.

With respect to this problem, incremental discovery has an advantage while generating <L,W> elementary patterns, because only one new sequence needs to be processed. Therefore, it is not wise to take the approach taken in the standard Teiresias algorithm and generate all combinations of elementary patterns over the alphabet. However, with incremental discovery, it makes sense to combinatorially generate all elementary patterns over the new input sequence. This is the approach taken in the algorithm of the present invention. The following pseudo code in Table 9 performs the job of generating all <L,W> candidate elementary patterns. The reason for calling them candidate elementary patterns is that whether there is support for these patterns has not yet been checked. The candidate elementary patterns become the actual elementary patterns once they have secured the required support (i.e., occur in at least K sequences, where K is the specified Teiresias parameter).

TABLE 9

For all seqlets given as input
Let s be the current seqlet.

TABLE 9-continued

For i from 1 to s.length-L
    For j from i+L to min(s.length, i+W)
        currentSlice = s.substring(i, j)
        numDots = j-i-L
        results +=
permuteDots (currentSlice, numDots)
    End For
End For
Scan results list and eliminate all strings that
do not begin
    and end with a character (not a dot)
Scan results list and eliminate duplicates
Return results In the pseudo code of table 9, s.length refers to the length of the string s and the function min(a, b) returns the minimum of a and b. The function s.substring(i, j) returns the substring of s between the indices i and j inclusive. A sub-routine called permuteDots is used. This is a recursive routine that generates all combinations of strings from the string parameter provided with don't care characters (dots) in it as per the other integer parameter. The pseudo code for permuteDots is given in Table 10. An example is provided infra.

TABLE 10 permuteDots (String slice, Integer nDots)
    results is a list
    If (nDots=0)
        results += slice
        return results
    End If
    If (nDots=1)
        For i from 1 to slice.length
            sliceCopy = new copy of slice
            results += sliceCopy.setAt(i, '.')
        End For
        return results
    End If
    For i from 1 to slice.length
        sliceCopy = new copy of slice
        sliceCopy.setAt(i, '.')
        List temp = permuteDots(slice.substring(i+1), nDots-1)
        For j from 1 to temp.length
            currentPattern = sliceCopy.substring(0, i+1) +
                temp[j]
            results += currentPattern
        End For
    End For
    return results
End permuteDots routine In the routine in Table 10, the parameter 'slice' is the string from which the elementary patterns are to be generated. The parameter 'nDots' specifies the maximum number of dots allowed in the generated patterns. The function slice.setAt(i, '.') sets the $i^{th}$ character of string 'slice' to a dot. Note that 'temp' variable in the pseudo code above is a list and temp.length gives the number of elements in that list and temp[j] returns the $j^{th}$ element of that list. For the seqlets provided as example in slicing step section 2.2, if L=2 and W=3, Table 11 shows the result of the process of the combinatorial generation step 23.

TABLE 11

| |
|---|
| Input Seqlets = {ATTG, TTGGGTG, TG, ACA, CCG} |
| Output Candidate Elementary Patterns = {AT, A.T, TT, T.G, TG, GG, G.G, G.T, GT, AC, A.A, CC, C.G, CG} |

The elementary patterns shown in Table 11 are the only elementary patterns that have any chance of generating any maximal Teiresias patterns due to the addition of $S_{n+1}$.

2.4 Check Support Step

In the check support step of FIG. 1, the candidate elementary patterns generated in the combinatorial generation step 23 is taken as input, and each candidate elementary pattern is checked against the sequence set S. If the candidate elementary pattern occurs in set S in at least (K−1) sequences then that pattern is marked as an elementary pattern. Since the pattern is present in $S_{n+1}$, a support of K−1 from the other sequences in set S is sufficient.

2.5 Convolve Step

Once the elementary patterns are generated in the check support step 24 of FIG. 1, the elementary patterns are grown in either direction, in the convolve step 25 of FIG. 1, to determine if maximal patterns with the required support can be obtained. A stack based convolve operation is carried out similar to the convolution process in the standard Teiresias algorithm described supra. This stack based implementation is described next in terms of only the salient features of the steps that are particular to the incremental Teiresias algorithm of the present invention.

Note the following two observations. The first observation is that before convolve the generated elementary patterns can be convolved, the patterns in $P_{next}$ is added to the pool of patterns that will be convolved. The reason for this is to grow the patterns by convolving them and therefore obtain maximal patterns. Clearly, the patterns in $P_{next}$ also should be taken into account for this purpose.

The second observation is that because of the addition of $S_{n+1}$ into the sequence set, there will be possibilities of some more specific versions of patterns from $P_{next}$ holding the required support. These more specific patterns should therefore be considered rather than their generic counterparts, if they hold the same support. Such specific patterns will not have a support more than their generic counterpart because if it were so, then Teiresias would in the first place not report the generic pattern at all (since it will then be non-maximal). This fact is utilized and a check is made to see if the specific patterns have a support equal to that of their generic counterpart. If the specific patterns do hold equal support, the generic pattern is discarded while the specific pattern is retained. If the specific patterns hold a support lesser that their generic counterpart then the specific patterns could be considered depending on whether they have at least K support, where K is the specified Teiresias parameter.

An aspect of generating these specific patterns is the order in which these specific patterns are generated and the tests for maximality that are made. The pseudo code in Table 12 gives a description of this part of the algorithm.

TABLE 12

| |
|---|
| Procedure specificPatterns<br>   specificResults is a global list<br>   For each $P_i$ in $P_{next}$<br>      For each $P_i^j$ occurrence of $P_i$<br>         generateSpecific ($P_i$, $P_i^j$)<br>      End For<br>   End For<br>   return specificResults<br>End procedure specificPatterns |

The iterations are performed over all occurrences of all patterns from the $P_{next}$ set. For each pattern occurrence, the function generateSpecific is called. The side-effect of calling this function is that the global list specificResults gets updated with more specific patterns that hold the required support. Here the pattern $P_i$ is the same as that in $P_{next}$, while $P_i^j$ is the exact occurrence of the pattern $P_i$ in $S_{n+1}$, which means that $P_i^j$ will not have any don't care characters (dots) at all. The pseudo code for generateSpecific function is in Table 13.

TABLE 13

| |
|---|
| Procedure generateSpecific (String specific, String generic)<br>   K` = support (generic)<br>   If (support (specific) =K` )<br>      If (isMaximal (specific))<br>         specificResults += specific<br>      End If<br>      Return<br>   End If<br>   If (support (specific) >=K)<br>      specificResults += specific<br>   End If<br>   List t = makeGenericByOne (specific, generic)<br>   For i from 1 to t.length<br>      generateSpecific (t [i], generic)<br>   End For<br>End Procedure generateSpecific |

In Table 13, K is the specified Teiresias parameter, and K' is the support of $P_i$. The above recursive procedure (i.e., generateSpecific calls itself) uses another procedure called makeGenericByOne, which looks at the specific pattern parameter, and provides a list of generic patterns that have one extra dot added in them in appropriate locations computed from the generic pattern parameter. The pseudo code for the makeGenericByOne procedure is given in Table 14.

TABLE 14

| |
|---|
| Procedure makeGenericByOne (String specific, String generic)<br>   t is a list<br>   num is a list<br>   For i from 1 to generic.length<br>      If (generic [i] = '.' AND specific [i] != '.')<br>         Add i to num list<br>      End If<br>   End For<br>   For i from 1 to num.length<br>      specificCopy = new copy of specific<br>      specificCopy.setAt (num [i], '.')<br>      Add specificCopy to t<br>   End For |

TABLE 14-continued return t
End Procedure makeGenericByOne

The patterns returned by the procedure specificPatterns and the elementary patterns from the check support step 24 are merged together and are given as input to the convolution process of step 25. The output of the convolution process of step 25 is a set of maximal patterns that are a result of the addition of the new sequence $S_{n+1}$. Note that the actual stack based convolution algorithm is the same as that in the standard Teiresias algorithm. Let the set of output patterns from the convolution step 25 be called $P_{increment}$.

2.6 Merge Step

The merge step 26 of FIG. 1 merges the newly generated patterns with the already generated Teiresias patterns as follows.

$$P'=P-P_{next}\cup P_{increment}$$

The patterns from $P_{next}$ are to be removed because they have been taken into consideration during the generation of the $P_{increment}$ patterns. The $P_{increment}$ is the result of the computation of new patterns as a result of the sequence $S_{n+1}$. Therefore, the final result is P'.

In summary, there is a given sequence set $S_1, S_2, \ldots, S_n$ and the corresponding Teiresias patterns P to start with. Then, an additional sequence $S_{n+1}$ is given to be added to the given sequence set. The problem is then to determine the new pattern set P' that reflects the addition of this additional sequence. One straightforward approach is to run the standard Teiresias algorithm again and rediscover all the patterns, which is more work than necessary. In contrast, the algorithm of the present invention computes these new patterns due to $S_{n+1}$ without running the standard Teiresias algorithm on the entire set, but to use the information that we have at hand (i.e., the already discovered patterns P) and perform only the incremental computation required to discover the new patterns.

There are various applications for the method of the present invention. These techniques of the present invention will be useful in scenarios where the sequences will be generated one after another, and there is a need to study the patterns as the sequences come by. In such scenarios, it makes more sense to have an incremental algorithm rather than running the original algorithm over the entire data set all the time. In clustering applications (for example in EST clustering, or Gene Sequencing), there will be occasions when a cluster would have its pattern set already discovered and new sequences might have to be added to the cluster, or that two clusters have to be merged. In such circumstances, the techniques of the present invention will be useful. In fact this technique can be used as a basis for clustering using Teiresias patterns.

The preceding applications of the incremental Teriresias pattern determinations (e.g., EST clustering, Gene Sequencing, etc.) may be implemented in accordance with the following iterative process for incrementally determining successive <L, W, K> Teiresias patterns associated with each of M successively added sequences to the base set S of sequences $S_1, S_2, \ldots, S_n$.

Let $S_{n+1}, S_{n+2}, \ldots, S_{n+M}$ denote the M succesively added sequences.

Let $S'_0$ denote the set S of $\{S_1, S_2, \ldots, S_n\}$, and $P'_0$ denotes the <L, W, K> Teiresias patterns from $S'_0$, wherein $P'_0$ has the same meaning as the pattern set P defined supra.

Let $S`_1 = S`_0 \cup S_{n+1}$, and $P`_1$ denotes the <L, W, K> Teiresias patterns from $S`_1$.
Let $S`_2 = S`_1 \cup S_{n+2}$, and $P`_2$ denotes the <L, W, K> Teiresias patterns from $S`_2$.

.
.
.

Let $S`_i = S`_{i-1} \cup S_{n+1}$, and $P`_i$ denotes the <L, W, K> Teiresias patterns from $S`_i$.

.
.
.

Let $S`_M = S`_{M-1} \cup S_{n+M}$, and $P`_M$ denotes the <L, W, K> Teiresias patterns from $S`_M$.

Accordingly, FIG. 3 is a flow chart with steps 51–56 describing a process for incrementally determining successive <L, W, K> Teiresias patterns associated with each of the M sequences successively added to the base set S of sequences $S_1, S_2, \ldots S_n$, Step 51 provides input to the incremental Teiresias algorithm, namely the sequence set $S'_0=S$, the positive integers L, K, and M, and the Teiresias patterns $P'_0$ denoting the <L, W, K> Teiresias patterns from $S'_0$.

Noting that i is a sequence index for the additional M sequences, step 52 sets i=1.

Step 53 provides the next sequence=$S_{n+i}$ and forms the set $S'_i=S'_{i-1}\cup S_{n+i}$.

Figure 4:
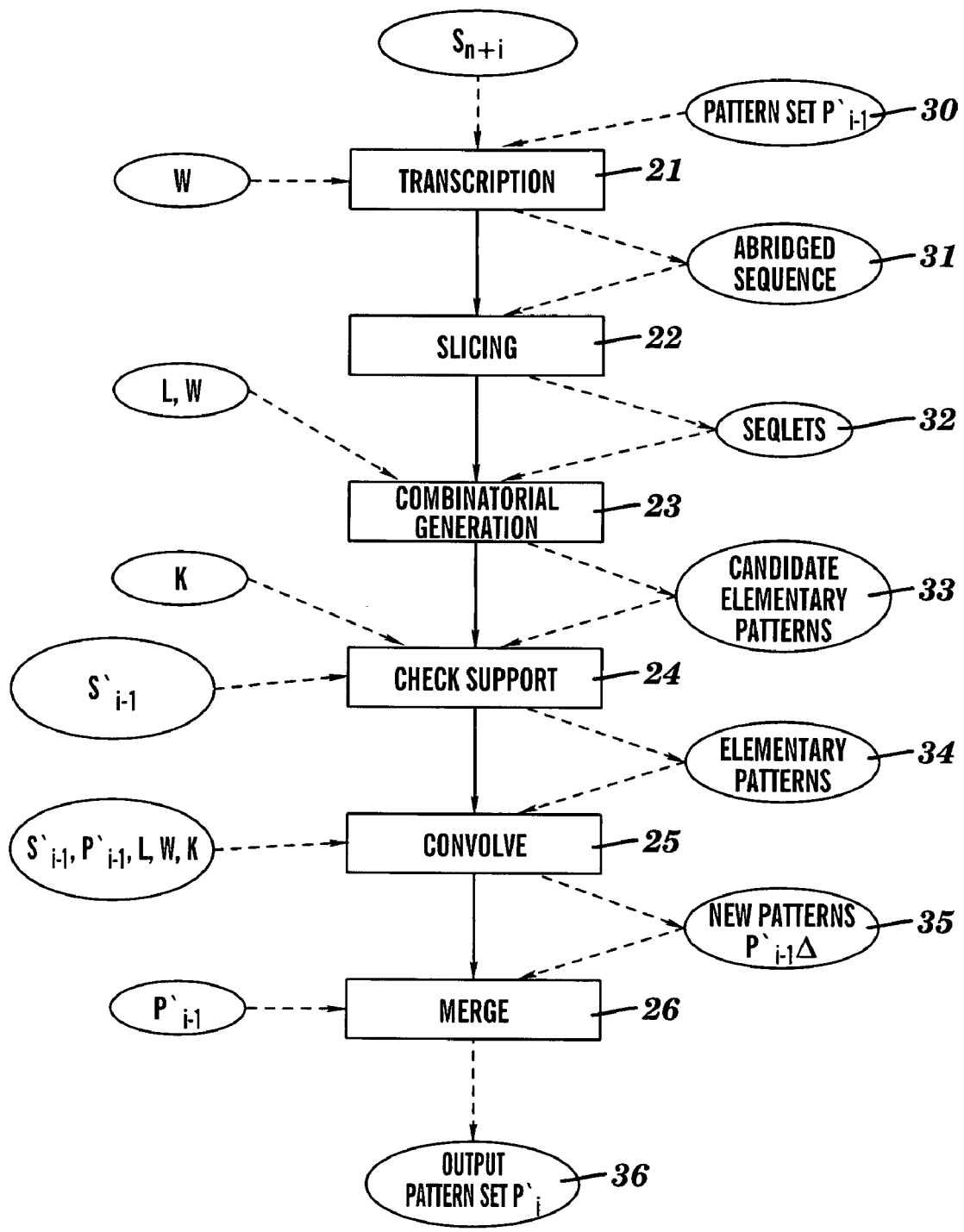
FIG. 4 is a modification of the high-level flow chart of FIG. 1 such that FIG. 4 represents a single iteration of the process described by the flow chart of FIG. 3, in accordance with embodiments of the present invention.
Figure 5:
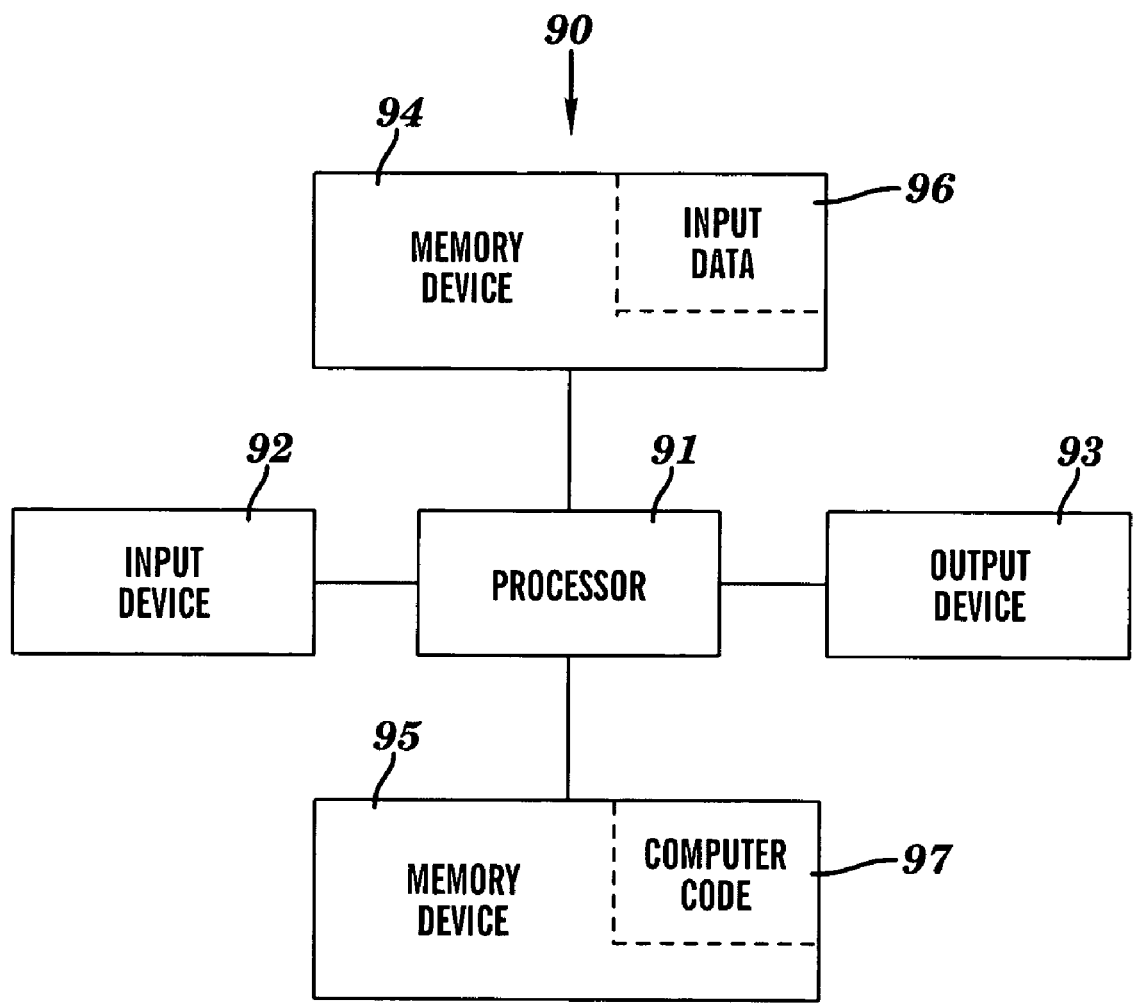
FIG. 5 illustrates a computer system used for incrementally determining Teiresias patterns, in accordance with embodiments of the present invention.

Step 54 incrementally determines the Teiresias patterns $P'_i$ for the set $S'_i$ by utilizing the set $S'_{i-1}$, L, W, K, $P'_{i-1}$, and $S_{n+i}$ as input, in accordance with the present invention (see FIG. 1 and the description thereof; see also FIG. 4 described infra).

Step 55 determines whether all of the additional M sequences have been processed (i.e., whether i=M).

If step 55 determines that all of the additional M sequences have been processed (i.e., i=M), then the process ends.

If step 55 determines that all of the additional M sequences have not been processed (i.e., i<M), then step 56 process increments i by 1 and the process loops back to step 53 to process the next sequence $S_{n+i}$.

FIG. 4 is a modification of the high-level flow chart of FIG. 1 such that FIG. 4 represents a single iteration, namely iteration i, of the process described by the flow chart of FIG. 3, in accordance with embodiments of the present invention. FIG. 4 is derived from FIG. 1 based on the following substitutions: $S_{n+1}$ is replace by $S_{n+i}$; P is replaced by $P'_{i-i}$; S is replaced by $S'_{i-i}$; and P' is replaced by $P'_i$.

3. Example of Incremental Determination of Teiresias Patterns

This section present an illustrated example of using the present invention to incrementally determine Teiresias patterns.

The following information is provided to the incremental Teiresias Algorithm as input. This includes the initial set of input sequences S, the pre-discovered Teiresias patterns P, the Teiresias parameters L, W and K, and the new sequences to be added to S (denoted as $S_{n+1}$; in this case $S_4$).

S = {S1=ABCDEFGHIJKLMNOPQRSTUV,
    S2=AXCDXXXHIJKLMNXXQTUV,
    S3=ABCDEFGHIJKLMNOPUAHIJKLMNOXYZSTUV
}
L=3; W=5; K=2
P = {   P1=HIJKLMN
        P2=TUV
        P3=A.CD
        P4=HIJKLMNO
        P5=ABCDEFGHIJKLMNOP
        P6=HIJKLMN...Q
        P7=STUV
        P8=HIJKLMN.X
}
S4=JSABCDEFGHIJKLMNOPQKLMAHUK

Each process of the algorithm specified in FIG. 1 is executed for the input data given supra. The output of each process is provided for better understanding.

3.1. Transcription (Step 21)

The inputs are pattern set P, the new sequence $S_4$, and the parameter W. The following are the intermediate results computed during this process.

$P_{next}$={P1, P3, P4, P5, P6}

TABLE 15

| $S_4$ | J | S | A | B | C | D | E | F | G | H | I | J | K | L | M | N | O | P | Q | K | L | M | A | H | U | K |
|---|---|---|---|---|---|---|---|---|---|---|---|---|---|---|---|---|---|---|---|---|---|---|---|---|---|---|
| $D_{in}$ | 0 | 0 | 2 | 0 | 0 | 0 | 0 | 0 | 0 | 3 | 0 | 0 | 0 | 0 | 0 | 0 | 0 | 0 | 0 | 0 | 0 | 0 | 0 | 0 | 0 | 0 |
| $D_{out}$ | 0 | 0 | 0 | 0 | 0 | 1 | 0 | 0 | 0 | 0 | 0 | 0 | 0 | 0 | 0 | 1 | 1 | 1 | 1 | 0 | 0 | 0 | 0 | 0 | 0 | 0 |
| i_p | 0 | 0 | 2 | 2 | 2 | 2 | 1 | 1 | 1 | 4 | 4 | 4 | 4 | 4 | 4 | 3 | 2 | 1 | 0 | 0 | 0 | 0 | 0 | 0 | 0 | 0 |
| tr | 1 | 1 | 1 | 1 | 1 | 1 | 0 | 0 | 0 | 0 | 0 | 0 | 0 | 0 | 0 | 1 | 1 | 1 | 1 | 1 | 1 | 1 | 1 | 1 | 1 | 1 |

Using the vectors above, the transcription algorithm will produce the following abridged sequence: JSABCDx-NOPQKLMAHUK.

3.2. Slicing (Step 22)

The input to this stage is the abridged-sequence shown above from transcription step 21. The output will be the following set of seqlets: {JSABCD, NOPQKLMAHUK}

3.3 Combinatorial Generation (Step 23)

Candidate elementary patterns are generated from the set of seqlets of the previous slicing process step 22. As explained supra, the candidate elementary patterns are not generated in a purely combinatorial fashion upon the entire alphabet set. Instead, the set of seqlets themselves are used as guide in generating the valid candidate elementary patterns. Table 16 comprises the list of candidate elementary patterns generated from this combinatorial generation step 23.

TABLE 16 candidate-elementary-patterns =
{   JSA, SAB, ABC, BCD,
    J.AB, S.BC, A.CD,
    JS.B, SA.C, AB.D,
    J..BC, S..CD,
    JS..C, SA..D,
    J.A.C, S.B.D,
    NOP, OPQ, PQK, QKL, KLM, LMA, MAH, AHU, HUK,
    N.PQ, O.QK, P.KL, Q.LM, K.MA, L.AH, M.HU, A.UK,
    NO.Q, OP.K, PQ.L, QK.M, KL.A, LM.H, MA.U, AH.K,
    NO..K, OP..L, PQ..M, QK..A, KL..H, LM..U, MA..K,
    N..QK, O..KL, P..LM, Q..MA, K..AH, L..HU, M..UK, TABLE 16-continued

N.P.K, O.Q.L, P.K.M, Q.L.A, K.M.H, L.A.U, M.H.K
}

3.4. Check Support (Step 24)

Out of these candidate-elementary-patterns obtained from the combinatorial generation step 23 and listed in Table 16, only those which have the requisite support given by the K parameter will be retained as elementary-patterns. In this example, K=2; therefore only those patterns from the above set that appears in at least one sequence apart from $S_4$ will be retained. The resultant elementary patterns are: {ABC, BCD, A.CD, AB.D, NOP, OPQ, KLM, N.PQ, NO.Q}

3.5. Convolve (Step 25)

The convolve step 25 performs the process where bigger patterns are generated from the elementary patterns obtained from the check support step 24. Also, in this convolve step 25, it is determined whether any of the patterns in the set $P_{next}$ becomes more specific as a result of the addition of $S_{n+1}$ into the sequence set. The only pattern that retains the required support even after making more specific from the set $P_{next}$ is $P_6$, because P6=HIJKLMN..Q becomes more specific to P6'=HIJKLMNOPQ and still holds K=2 support.

Therefore, the set of patterns given to the convolution process is the union of elementary-patterns, $P_{next}$ and $P_6'$, as shown below as convolution-input-patterns =
{   ABC, BCD, A.CD, AB.D, NOP, OPQ, KLM, N.PQ, NO.Q,
    HIJKLMN, TUV, A.CD, HIJKLMNO,
    ABCDEFGHIJKLMNOP,
    HIJKLMN..Q, HIJKLMNOPQ, STUV,
    HIJKLMN.X
}

The output of the convolution process is the following set $P_{increment}$ of patterns:

$P_{increment}$ = {ABCDEFGHIJKLMNOP, ABCDEFGHIJKLMNOPQ
    HIJKLMN, A.CD, HIJKLMNO,
    HIJKLMN..Q, KLM
}

3.6. Merge (Step 26):

The incrementally calculated patterns are merged with the original set as follows.

```
P` = P - P_next ∪ P_increment.
Therefore, P` = {P1=HIJKLMN
                 P2=TUV
                 P3=A.CD
                 P4=HIJKLMNO
                 P5=ABCDEFGHIJKLMNOP
                 P6=HIJKLMN..Q
                 P7=STUV
                 P8=HIJKLMN.X
                 P9=ABCDEFGHIJKLMNOPQ
                 P10=KLM
                }
```

The pattern set P' is the final output of the algorithm. Note that the original Teiresias algorithm has been run on the input set S={S1, S2, S3, S4}, which resulted in computed output patterns matching the output patterns P' obtained by the previous calculations in accordance with the algorithm of the present invention. This verifies the correctness of the algorithm of the present invention.

4. Computer System

FIG. 4 illustrates a computer system 90 used for incrementally determining Teiresias patterns, in accordance with embodiments of the present invention. The computer system 90 comprises a processor 91, an input device 92 coupled to the processor 91, an output device 93 coupled to the processor 91, and memory devices 94 and 95 each coupled to the processor 91. The input device 92 may be, inter alia, a keyboard, a mouse, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes an algorithm for incrementally determining Teiresias patterns. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices not shown in FIG. 4) may be used as a computer usable medium (or a computer readable medium or a program storage device) having a computer readable program code embodied therein and/or having other data stored therein, wherein the computer readable program code comprises the computer code 97. Generally, a computer program product (or, alternatively, an article of manufacture) of the computer system 90 may comprise said computer usable medium (or said program storage device).

Thus the present invention discloses a process for deploying or integrating computing infrastructure, comprising integrating computer-readable code into the computer system 90, wherein the code in combination with the computer system 90 is capable of performing a method that incrementally determines Teiresias patterns.

While FIG. 4 shows the computer system 90 as a particular configuration of hardware and software, any configuration of hardware and software, as would be known to a person of ordinary skill in the art, may be utilized for the purposes stated supra in conjunction with the particular computer system 90 of FIG. 4. For example, the memory devices 94 and 95 may be portions of a single memory device rather than separate memory devices.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A method for determining Teiresias patterns, said method comprising the steps of:
providing a set $S'_0$ of n sequences denoted as $S_1, S_2, \ldots S_n$, positive integers L, W, and K, and Teiresias patterns $P'_0$ consisting of all <L, W, K> patterns for the set $S'_0$, each sequence of the n sequences consisting of characters from an alphabet, wherein a sequence index i equals 1;
supplying a sequence $S_{n+1}$ to form a set $S'_i$ consisting of $S'_{i-1} \cup S_{n+1}$, wherein $S_{n+1}$ consists of characters from the alphabet; and
determining Teiresias patterns $P'_i$ consisting of all <L, W, K> patterns for the set $S'_i$ by performing an algorithm that utilizes $S'_{i-1}$, L, W, K, $P'_{i-1}$, and $S_{n+i}$ as input.

2. The method of claim 1, said method further comprising the step of: ascertaining whether there is an additional sequence to be processed, and if said ascertaining ascertains that there is not said additional sequence is to be processed then ending said method else incrementing i by 1 followed by performing said supplying, determining, and ascertaining steps, said ascertaining step being performed after said determining step.

3. The method of claim 2, wherein a first performance of said ascertaining step ascertains that there is not said additional sequence is to be processed.

4. The method of claim 2, wherein a first performance of said ascertaining step ascertains that there is said additional sequence is to be processed.

5. The method of claim 1, wherein providing $P'_0$ comprises determining $P'_0$ by performing a standard Teiresias algorithm.

6. The method of claim 1, wherein providing $P'_0$ does not comprise determining $P'_0$ by performing a standard Teiresias algorithm.

7. The method of claim 1, wherein performing the algorithm comprises:
performing a transcription step that utilizes W, $P'_{i-1}$, and $S_{n+i}$ as input and outputs an abridged sequence;
performing a slicing step that utilizes the abridged sequence as input and outputs seqlets;
performing a combinatorial generation step that utilizes L, W, and the seqlets as input and outputs candidate elementary patterns;
performing a check support step that utilizes $S'_{i-1}$, K, and the candidate elementary patterns as input and outputs elementary patterns;
performing a convolve step that utilizes $S'_{i-1}$, $P'_{i-1}$, L, W, K and the elementary patterns as input and outputs new patterns $P'_{i-1}\Delta$; and
performing a merge step that utilizes $P'_{i-1}$ and the new patterns $P'_{i-1}\Delta$ as input and outputs $P'_i$.

8. The method of claim 1, wherein the alphabet is a nucleotide alphabet.

9. The method of claim 1, wherein each character is a residue of a molecular structure.

10. The method of claim 1, said method further comprising the step of: utilizing $P'_i$ in gene sequencing or in express sequence tags (EST) clustering, said utilizing step being performed after said determining step.

11. A computer program product, comprising a computer usable medium having a computer readable program code embodied therein, said computer readable program code comprising an algorithm adapted to implement a method for determining Teiresias patterns, said method comprising the steps of:

providing a set $S'_0$ of n sequences denoted as $S_1, S_2, \ldots S_n$, positive integers L, W, and K, and Teiresias patterns $P'_0$ consisting of all <L, W, K> patterns for the set $S'_0$, each sequence of the n sequences consisting of characters from an alphabet, wherein a sequence index i equals 1;

supplying a sequence $S_{n+1}$ to form a set $S'_i$ consisting of $S'_{i-1} \cup S_{n+1}$, wherein $S_{n+1}$ consists of characters from the alphabet; and determining Teiresias patterns $P'_i$ consisting of all <L, W, K> patterns for the set $S'_i$ by performing an algorithm that utilizes $S'_{i-1}$, L, W, K, $P'_{i-1}$, and $S_{n+i}$ as input.

12. The computer program product of claim 11, said method further comprising the step of:

ascertaining whether there is an additional sequence to be processed, and if said ascertaining ascertains that there is not said additional sequence is to be processed then ending said method else incrementing i by 1 followed by performing said supplying, determining, and ascertaining steps, said ascertaining step being performed after said determining step.

13. The computer program product of claim 12, wherein a first performance of said ascertaining step ascertains that there is not said additional sequence is to be processed.

14. The computer program product of claim 12, wherein a first performance of said ascertaining step ascertains that there is said additional sequence is to be processed.

15. The computer program product of claim 11, wherein providing $P'_0$ comprises determining $P'_0$ by performing a standard Teiresias algorithm.

16. The computer program product of claim 11, wherein providing $P'_0$ does not comprise determining $P'_0$ by performing a standard Teiresias algorithm.

17. The computer program product of claim 11, wherein performing the algorithm comprises:

performing a transcription step that utilizes W, $P'_{i-1}$, and $S_{n+i}$ as input and outputs an abridged sequence;

performing a slicing step that utilizes the abridged sequence as input and outputs seqlets;

performing a combinatorial generation step that utilizes L, W, and the seqlets as input and outputs candidate elementary patterns;

performing a check support step that utilizes $S'_{i-1}$, K, and the candidate elementary patterns as input and outputs elementary patterns;

performing a convolve step that utilizes $S'_{i-1}$, $P'_{i-1}$, L, W, K and the elementary patterns as input and outputs new patterns $P'_{i-1}\Delta$; and performing a merge step that utilizes $P'_{i-1}$ and the new patterns $P'_{i-1}\Delta$ as input and outputs $P'_i$.

18. The computer program product of claim 11, wherein the alphabet is a nucleotide alphabet.

19. The computer program product of claim 11, wherein each character is a residue of a molecular structure.

20. The computer program product of claim 11, said method further comprising the step of:

utilizing $P'_i$ in gene sequencing or in express sequence tags (EST) clustering, said utilizing step being performed after said determining step.

21. A process for integrating computing infrastructure, said process comprising integrating computer-readable code into a computing system, wherein the code in combination with the computing system is capable of performing a method for determining Teiresias patterns, said method comprising the steps of:

providing a set $S'_0$ of n sequences denoted as $S_1, S_2, \ldots S_n$, positive integers L, W, and K, and Teiresias patterns $P'_0$ consisting of all <L, W, K> patterns for the set $S'_0$, each sequence of the n sequences consisting of characters from an alphabet, wherein a sequence index i equals 1;

supplying a sequence $S_{n+1}$ to form a set $S'_i$ consisting of $S'_{i-1} \cup S_{n+1}$, wherein $S_{n+1}$ consists of characters from the alphabet; and determining Teiresias patterns $P'_i$ consisting of all <L, W, K> patterns for the set $S'_i$ by performing an algorithm that utilizes $S'_{i-1}$, L, W, K, $P'_{i-1}$, and $S_{n+i}$ as input.

22. The process of claim 21, said method further comprising the step of: ascertaining whether there is an additional sequence to be processed, and if said ascertaining ascertains that there is not said additional sequence is to be processed then ending said method else incrementing i by 1 followed by performing said supplying, determining, and ascertaining steps, said ascertaining step being performed after said determining step.

23. The process of claim 22, wherein a first performance of said ascertaining step ascertains that there is not said additional sequence is to be processed.

24. The process of claim 22, wherein a first performance of said ascertaining step ascertains that there is said additional sequence is to be processed.

25. The process of claim 21, wherein providing $P'_0$ comprises determining $P'_0$ by performing a standard Teiresias algorithm.

26. The process of claim 21, wherein providing $P'_0$ does not comprise determining $P'_0$ by performing a standard Teiresias algorithm.

27. The process of claim 21, wherein performing the algorithm comprises:

performing a transcription step that utilizes W, $P'_{i-1}$, and $S_{n+i}$ as input and outputs an abridged sequence;

performing a slicing step that utilizes the abridged sequence as input and outputs seqlets;

performing a combinatorial generation step that utilizes L, W, and the seqlets as input and outputs candidate elementary patterns;

performing a check support step that utilizes $S'_{i-1}$, K, and the candidate elementary patterns as input and outputs elementary patterns;

performing a convolve step that utilizes $S'_{i-1}$, $P'_{i-1}$, L, W, K and the elementary patterns as input and outputs new patterns $P'_{i-1}\Delta$; and performing a merge step that utilizes $P'_{i-1}$ and the new patterns $P'_{i-1}\Delta$ as input and outputs $P'_i$.

28. The process of claim 21, wherein the alphabet is a nucleotide alphabet.

29. The process of claim 21, wherein each character is a residue of a molecular structure.

30. The process of claim 21, said method further comprising the step of: utilizing $P'_i$ in gene sequencing or in express sequence tags (EST) clustering, said utilizing step being performed after said determining step.

* * * * *